(12) United States Patent
Phinney et al.

(10) Patent No.: US 6,868,135 B1
(45) Date of Patent: Mar. 15, 2005

(54) METHOD AND APPARATUS FOR CORRECTING FOR A PHASE SHIFT BETWEEN A TRANSMITTER AND A RECEIVER

(75) Inventors: Daniel P. Phinney, Rochester, NY (US); Albert H. Titus, Batavia, NY (US)

(73) Assignees: Eastman Kodak Company, Rochester, NY (US); Rochester Institute of Technology, Rochester, NY (US)

( * ) Notice: Subject to any disclaimer, the term of this patent is extended or adjusted under 35 U.S.C. 154(b) by 0 days.

(21) Appl. No.: 09/573,914

(22) Filed: May 18, 2000

(51) Int. Cl.$^7$ ............................................. H04L 25/40
(52) U.S. Cl. ..................... 375/371; 375/219; 375/259; 375/224; 455/73; 455/113; 455/125; 455/139; 455/316; 455/340; 331/25; 331/179; 327/231; 324/76.41; 324/76.52; 324/76.77
(58) Field of Search ................................ 375/221, 219, 375/224, 259, 371; 455/73, 75, 113, 125, 139, 316, 340; 331/25, 179; 327/231–234, 236, 237, 243, 244; 324/76.41, 76.52, 76.77

(56) References Cited

U.S. PATENT DOCUMENTS

| | | | |
|---|---|---|---|
| 3,663,956 A | | 5/1972 | Purdy et al. |
| 3,754,207 A | * | 8/1973 | Delignieres ................. 367/87 |
| 3,953,794 A | | 4/1976 | Moore |
| 4,066,969 A | | 1/1978 | Pearce et al. |
| 4,370,574 A | | 1/1983 | Nielsen |
| 4,400,664 A | | 8/1983 | Moore |
| 4,408,165 A | | 10/1983 | Braun |
| 4,425,543 A | | 1/1984 | Adams et al. |
| 4,600,994 A | | 7/1986 | Hayashi |
| 4,607,218 A | | 8/1986 | Stosel |
| 4,775,890 A | | 10/1988 | Balaban et al. |
| 4,963,817 A | | 10/1990 | Kohiyama et al. |
| 5,151,638 A | | 9/1992 | Beckerman |
| 5,266,851 A | | 11/1993 | Nukui |
| 5,432,826 A | | 7/1995 | Rieder |
| 5,438,254 A | | 8/1995 | Ho et al. |
| 5,481,198 A | | 1/1996 | Patel |
| 5,506,874 A | | 4/1996 | Izzard et al. |
| 5,568,071 A | | 10/1996 | Hoshino et al. |
| 5,583,458 A | | 12/1996 | Bazes |
| 5,604,768 A | * | 2/1997 | Fulton ........................ 375/220 |
| 5,619,148 A | | 4/1997 | Guo |
| 5,818,265 A | | 10/1998 | Meller et al. |
| 5,903,605 A | | 5/1999 | Crittenden |
| 5,949,260 A | | 9/1999 | Toda |

* cited by examiner

Primary Examiner—Tesfaldet Bocure
Assistant Examiner—Pankaj Kumar
(74) Attorney, Agent, or Firm—Nelson Adrian Blish

(57) ABSTRACT

A method and apparatus for correcting for a phase shift between a transmitter and receiver comprising the steps of:
   a) transmitting a signal from a transmitter (14);
   b) receiving the transmitted signal (16) at a receiver (20);
   c) comparing the received signal (17) to a reference signal;
   d) if a difference between the reference signal and the received signal (17) is greater than a predetermined value go to step e), if not go to step g);
   e) adjusting a frequency of the transmitted signal (16);
   f) go to step a); and
   g) calibration complete.

9 Claims, 10 Drawing Sheets

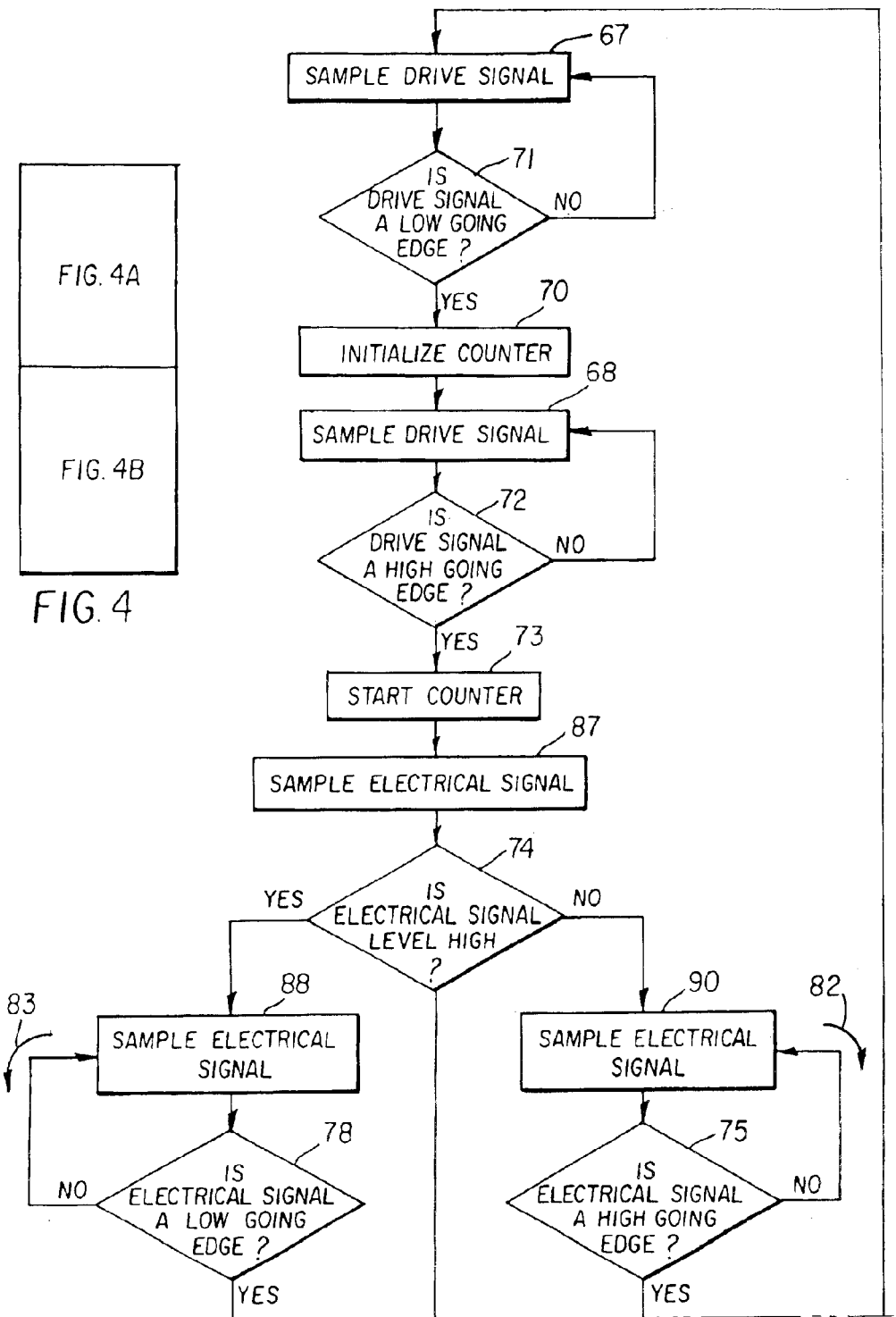

METHOD AND APPARATUS FOR CORRECTING FOR A PHASE SHIFT BETWEEN A TRANSMITTER AND A RECEIVER

FIELD OF THE INVENTION

This invention relates in general to phase shift calibration by electronic means and in particular, to calibration of ultrasonic detectors for multiple document feeds.

BACKGROUND OF THE INVENTION

Scanners and copiers use document feeders to transport documents into the machine. Mechanisms used for the transportation of documents, including paper or sheets of other material, have the capacity to accidentally pick up more than one document fed from a stack of documents. It is necessary to determine when more than one document is pulled into a document transport since multiple documents may jam the transport or prevent processing some documents.

A non-contact method for multiple document detection sends ultrasound signals through the document stream to determine if more than one document is present. Sending ultrasound through paper results in attenuation of the ultrasound signal. It is possible to determine the presence of multiple documents by measuring the phase shift ultrasound signal passing through documents. See U.S. Pat. No. 4,066,969 which is herein incorporated by reference. As ultrasound passes from the ultrasonic transmitter to the ultrasonic receiver, the phase changes, depending on the wavelength and the distance.

Due to vibrations, temperature changes, or usage, the distance between a transmitter and a receiver can change over time. It is often desirable to have the signal at the receiver in phase with the signal at the transmitter. In order to make this happen, the distance between the transmitter and receiver must be physically changed by moving one or the other or both. This requires moving parts that require physical space and that will eventually wear out. It would be highly desirable to calibrate ultrasonic detectors electronically.

SUMMARY OF THE INVENTION

According to one aspect of the present invention, a method for correcting for a phase shift between a transmitter and receiver comprises the steps of:

a) transmitting a signal from a transmitter;
b) receiving the transmitted signal at a receiver;
c) comparing the received signal to a reference signal;
d) if a difference between the reference signal and the received signal is greater than a predetermined value go to step e), if not go to step g);
e) adjusting a frequency of said transmitted signal;
f) go to step a); and
g) calibration complete.

An advantage of the present invention is that it eliminates the manual process and related mechanical parts to perform a calibration of ultrasonic detectors.

A method for adjusting phase in accordance with another embodiment of the present invention includes a few steps. First, a phase difference between a transmitted signal and a received signal resulting from the transmitted signal is determined. Once the phase difference is determined, the frequency of the transmitted signal is adjusted in response to the determined phase difference so that an adjusted phase difference between the transmitted signal and the received signal is less than a first set phase difference.

An apparatus for adjusting phase in accordance with another embodiment of the present invention includes a transmitter, a receiver, and a phase adjustor. The transmitter sends out a transmitted signal at a frequency. The receiver captures a received signal resulting from the transmitted signal. The phase adjustor determines a phase difference between the transmitted signal and the received signal and adjusts the frequency of the transmitted signal so that an adjusted phase difference between the transmitted signal and the received signal is less than a first set phase difference.

An advantage of the present invention is that it eliminates the manual process and related mechanical parts to perform a calibration of ultrasonic detectors. With the present invention, recalibration can be carried out automatically on a periodic basis when document detection is not being carried out.

Another advantage of the present invention is that it can be used in any system that requires zero phase difference between the transmitted and received signals.

Yet another advantage of the present invention is that the phase detection system can be used for any transmitted and received signal wherein the phase is a fixed difference other than zero.

The invention and its objects and advantages will become more apparent in the detailed description of the preferred embodiment presented below.

DETAILED DESCRIPTION OF THE INVENTION

Figure 12:
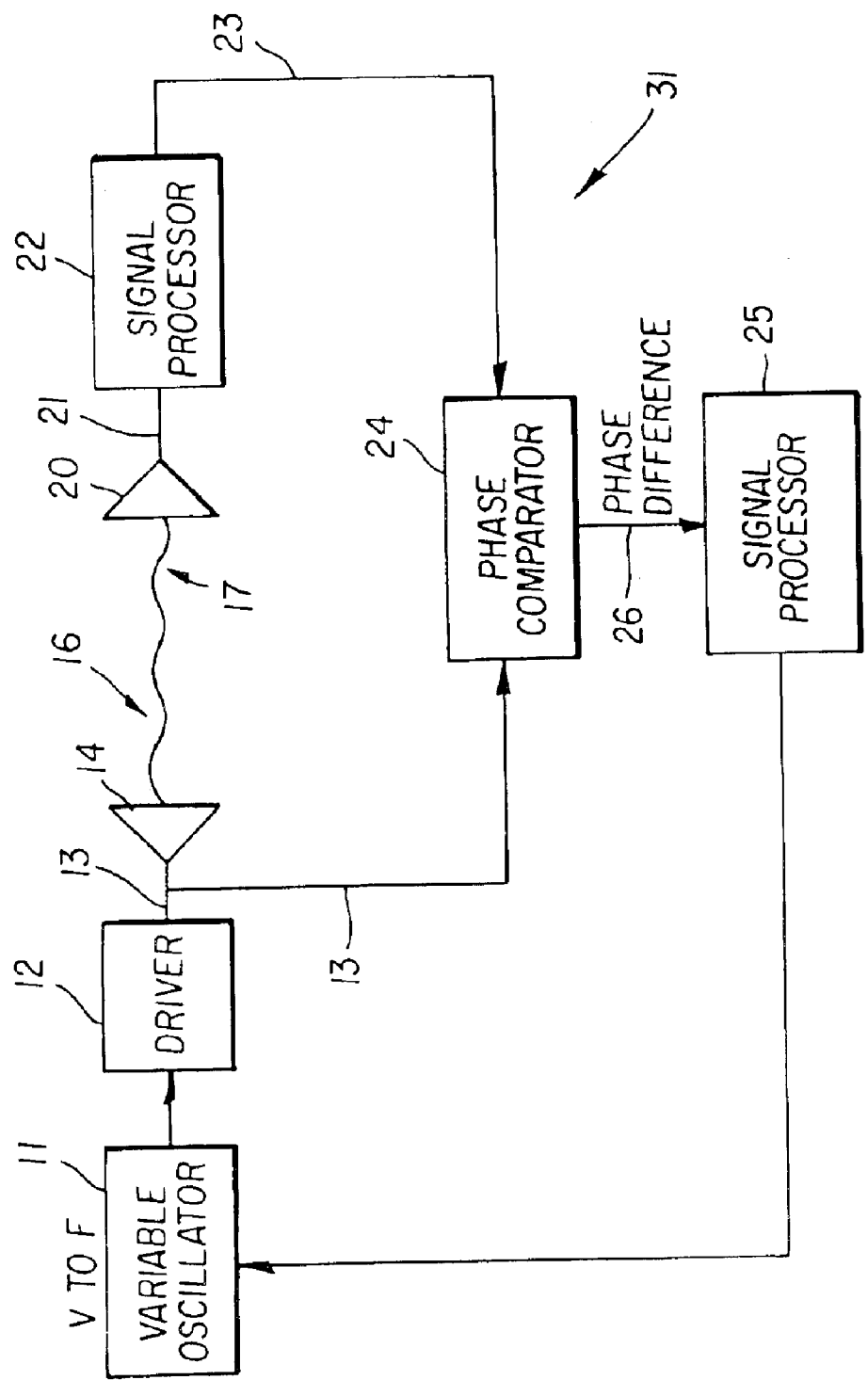
FIG. 12 is a block diagram of a circuit for correcting a phase shift between a transmitter and a receiver in accordance with another embodiment of the present invention.

An apparatus 31 for correcting for a phase shift in accordance with one embodiment of the present invention is illustrated in FIG. 12. The apparatus 31 for correcting a phase shift includes a transmitter 14, a receiver 20, and a phase adjustor. The transmitter 14 sends out a transmitted signal at a frequency. The receiver 20 captures a received signal resulting from the transmitted signal. The phase adjustor determines a phase difference between the transmitted signal and the received signal and adjusts the frequency of the transmitted signal so that an adjusted phase difference between the transmitted signal and the received signal is less than a first set phase difference. A method for correcting phase shift in accordance with one embodiment carries out the steps set forth in the apparatus above. The apparatus and method for correcting phase shift provide a number of advantages including providing a simple and automatic technique for adjusting the phase difference between a transmitted signal and a received signal.

Figure 1:
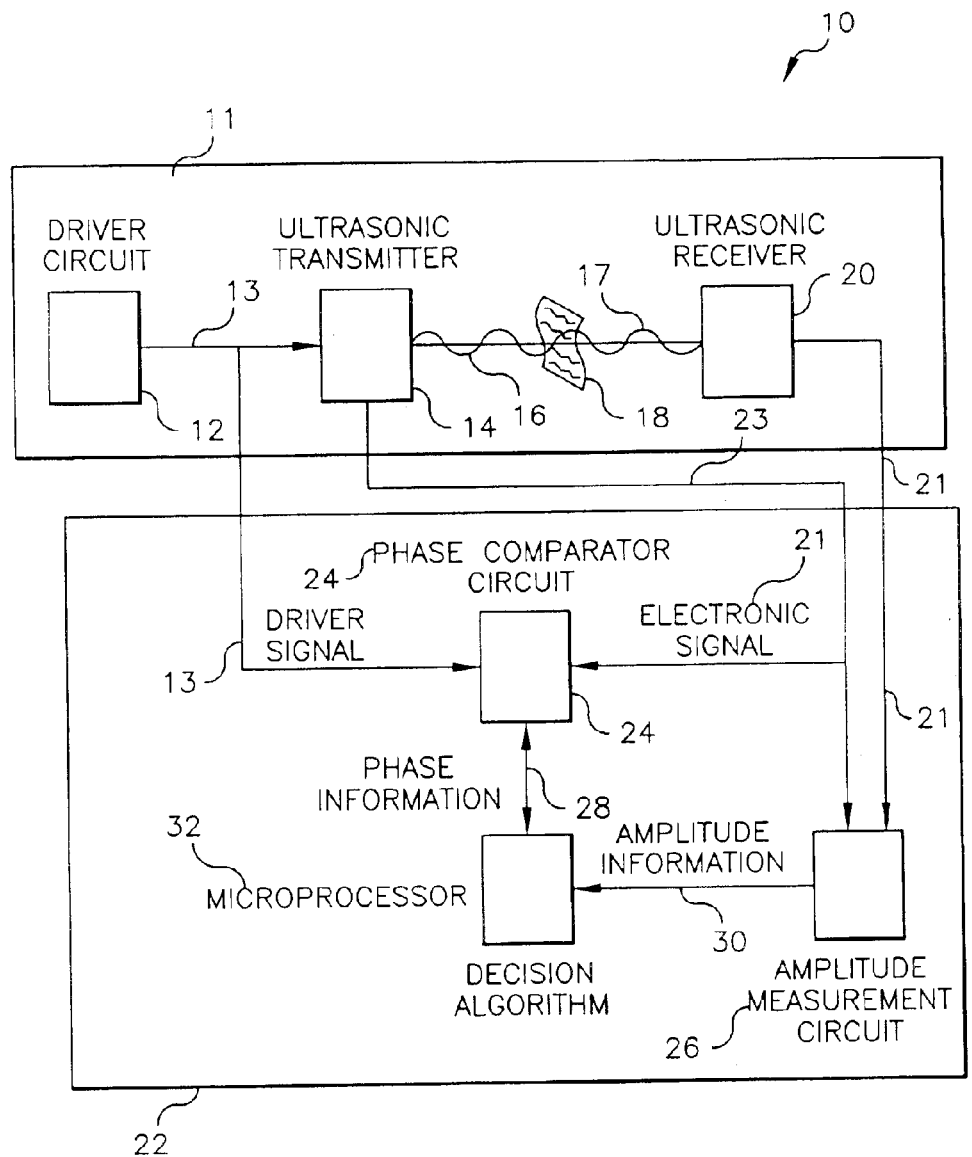
FIG. 1 is a block diagram of detection circuit using phase shift measurement in accordance with one embodiment of the present invention.

Referring to FIG. 1, an apparatus 10 for multiple document detection in accordance with one embodiment of the present invention is shown. In this particular embodiment, the apparatus 10 includes an ultrasonic drive circuit 12 which provides a drive signal 13 to an ultrasonic transmitter 14. The ultrasonic transmitter 14 produces an ultrasonic signal 16 that passes through a document feed 18 which comprises one or more documents and is received by an ultrasonic receiver 20. A phase shift of the ultrasonic signal 16 is relatively independent of the thickness of the document or documents in the document feed 18. This results in a received ultrasonic signal 17 with a phase shift approximately dependent on only the number of documents in the document feed 18, because of the interfaces between different materials through which the ultrasound passes causes the phase shift, not the total thickness of the documents.

The ultrasonic receiver 20 converts the received ultrasonic signal 17 into an electrical signal 21. The electronic signal 21 is supplied to an input to a phase comparator 24 where the phase difference between the drive signal 13 and the electrical signal 21 is determined as explained in greater detail below with references to FIGS. 3–5. An information signal 28 which represents the determined phase difference is fed from phase comparator 24 to a microprocessor 32. The microprocessor 32 monitors information signal 28 to determine if multiple documents are present based on the resulting phase shift or difference between the drive signal 13 and the electrical signal 21. Although a microprocessor 32 is shown, other types of processors or programmable devices can also be used. Additionally, although in this particular example an ultrasonic signal is used in this apparatus 10, other types of signals, such as electromagnetic, can also be used.

Figure 2:
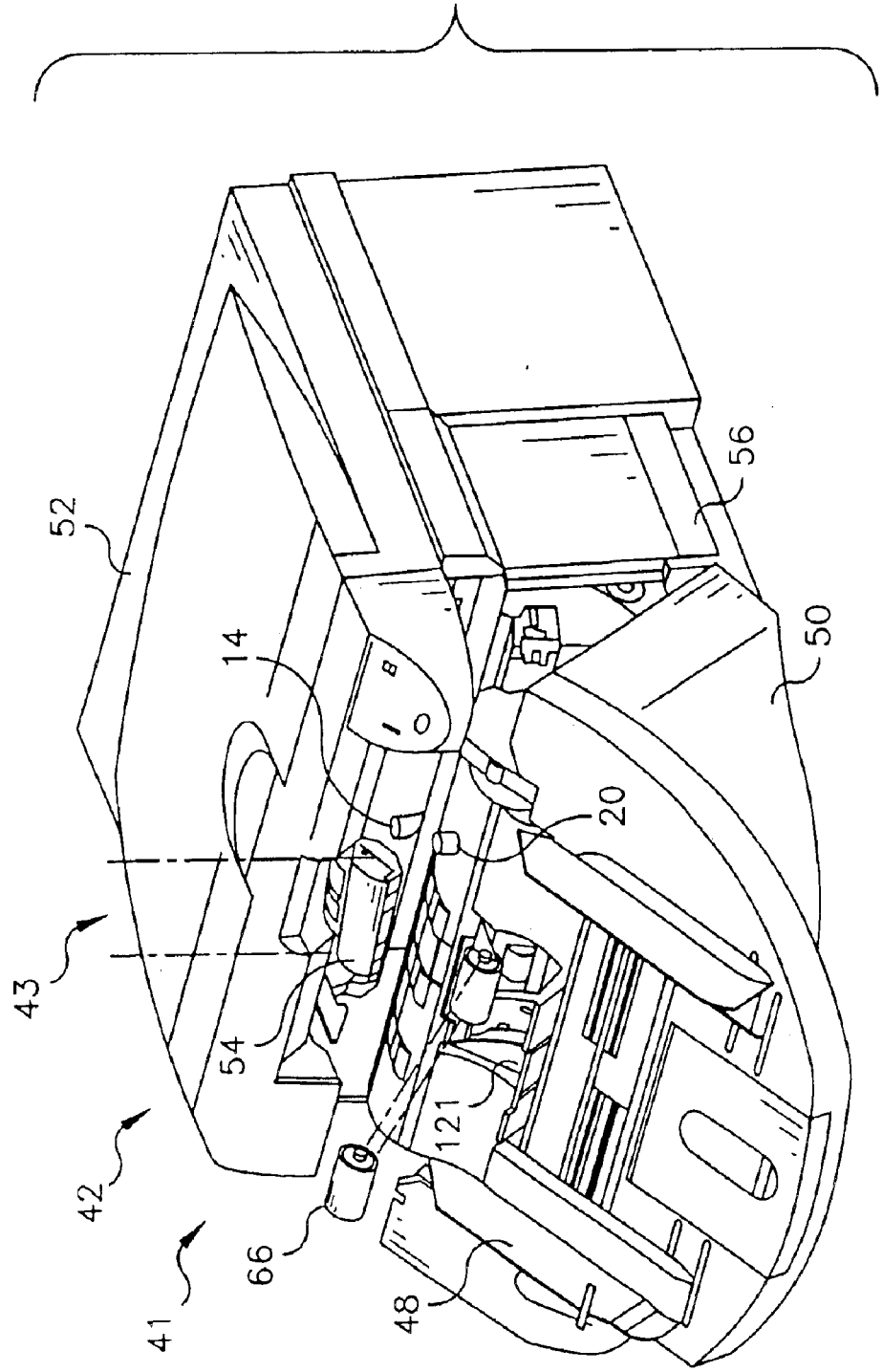
FIG. 2 is a perspective view of a typical sheet feeding device.

Referring to FIG. 2, a typical device employing a document transport, in this case a sheet feeder, is shown. In this particular embodiment, the sheet feeding device 42 comprises a stack support 48 disposed in a first portion 50 of a housing 52. A feed module 54 is detachably mounted in a second portion 56 of the housing 52 so as to be in contact with a stack of documents. Separator 66 is a mechanical device for reducing multiple feeds. Ultrasonic transmitter 14 and ultrasonic receiver 20 are positioned so that documents are transported between them after the documents leave the stack. Other locations in the document transport system may also be suitable for positioning the ultrasonic transmitter 14 and receiver 20. Multiple documents which are not physically separated by separator 66 are detected above.

The present invention provides a digital method and apparatus to obtain a phase difference measurement without the need for any analog processing. The phase difference between two signals can be determined digitally by measuring the time difference of the zero or other set level crossover point or location of these two signals. Alternately, the phase difference can be determined from the time differences of the high going or low going edges of these two signals.

Figure 3:
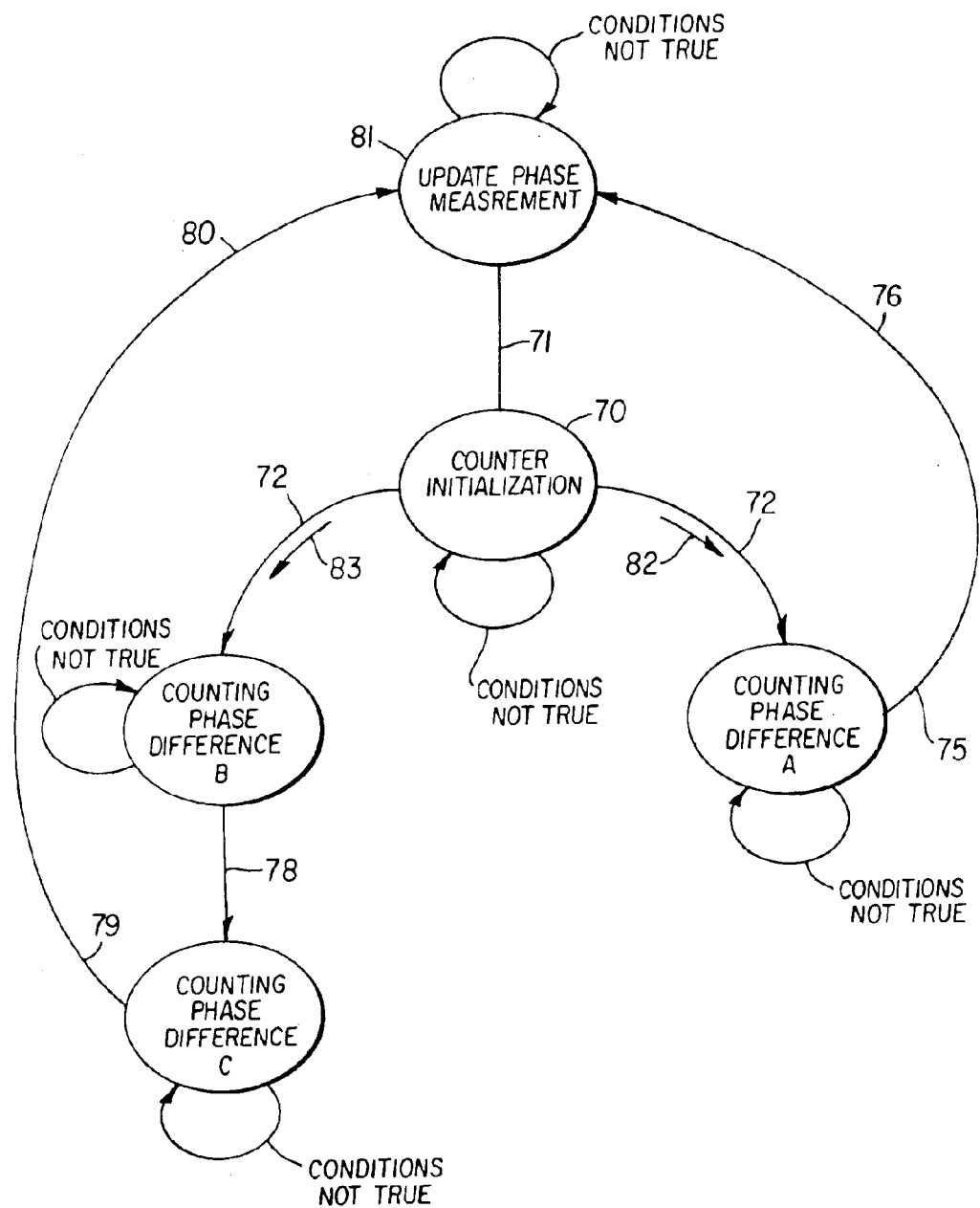
FIG. 3 is a state diagram of an algorithm used for determination of phase shift according to one embodiment of the present invention.
Figure 4B:
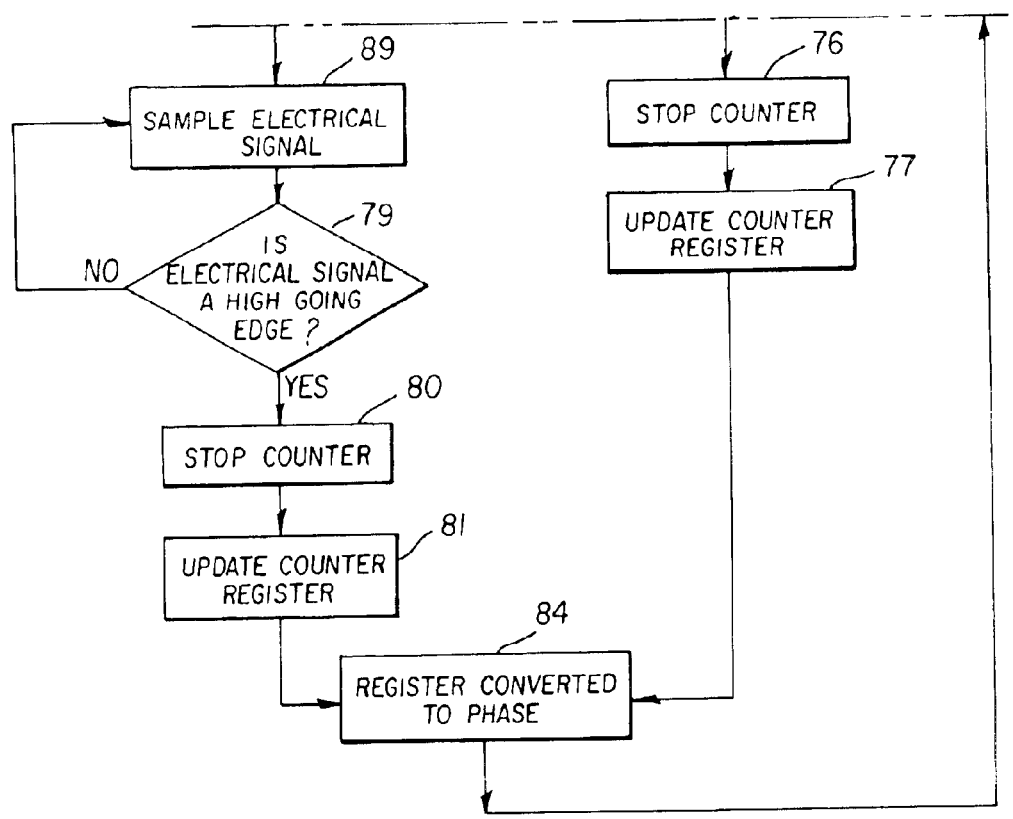
FIG. 4 is a flow chart for phase shift detection for the state diagram shown in FIG. 3.
Figure 5:
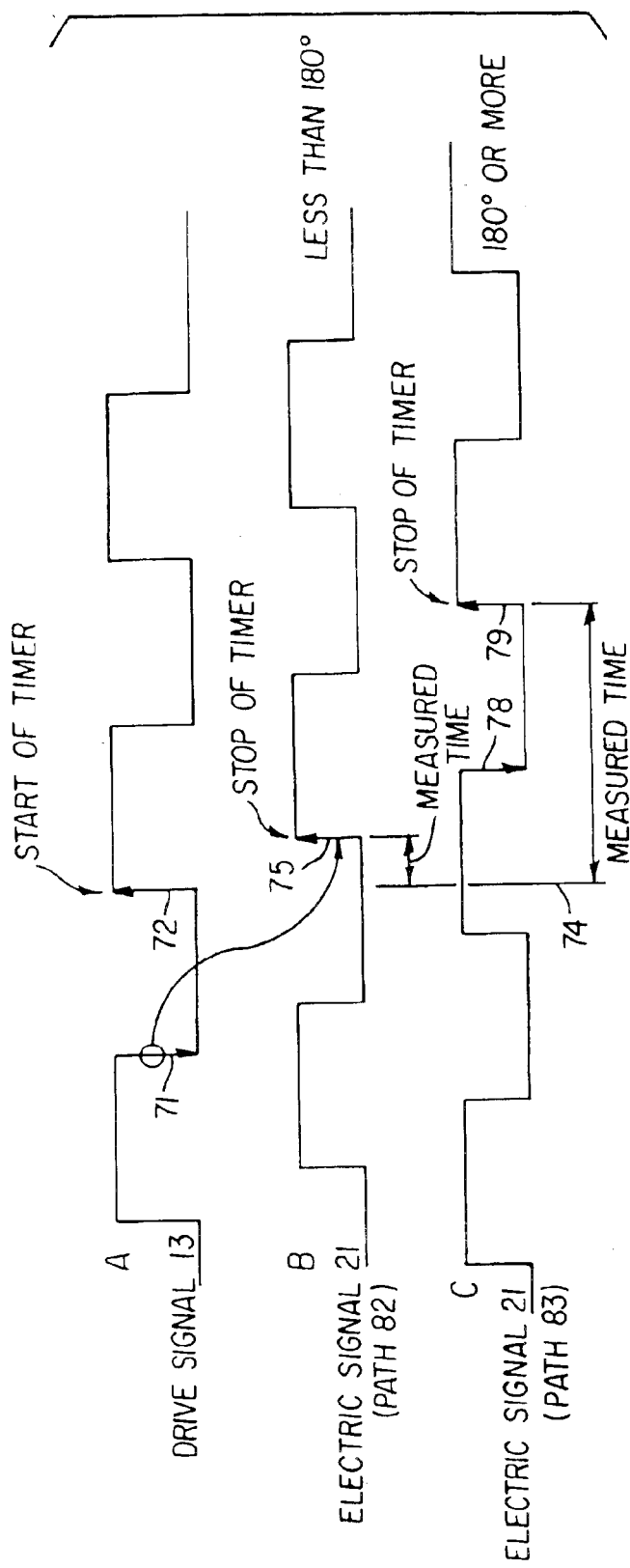
FIG. 5 are wave forms showing a phase shift.

Referring to FIGS. 3–5, a method in accordance with one embodiment of the present invention is illustrated. In this particular embodiment, the drive signal 13 is used as a reference signal and is sampled 67. If a low going level is detected 71 the counter is initialized 70. If a lower going edge is not detected the drive signal is sampled again 67.

After the counter is initialized, the drive signal is sampled again 68. If a high going edge is not detected the drive signal 13 is resampled 68. When a high going edge is detected 72 the counter is started 73.

The electrical signal 21 is sampled 87. If the electrical signal level is at a high level, path 83 is selected and the electrical signal 21 is sampled 88. If a low going edge is not detected 78, sampling continues 88. When low going edge is detected 78 sampling of the electrical signal 21 continues 89.

The reason for detecting a low going edge is shown by reference to wave form A and wave form C in FIG. 5. Since the level of the electric signal is high there is the possibility that the high going edge of the electric signal 21 and the drive signal 13 could coincide so the first low going edge must be detected, which is shown schematically by the total measured time. Thus, phase differences greater than one half cycle may be measured.

Sampling of the electrical signal 21 continues at step 89 until a high going edge is detected 79. At this point the counter is stopped 80 and the counter register value is updated 81. If a high going edge is not detected the electrical signal 21 is resampled 89. The counter register 81 is converted to an actual phase value 84 by a microprocessor and the drive signal is again sampled 67 for a low going edge.

If the electrical level is not high 74, path 82 is selected and the electrical signal is sampled 90 for a high going edge. When a high going edge is detected 75 the counter is stopped 76 and the counter register is updated 77. If a high going edge is not detected 75 the electrical signal is resampled 90. When the counter register is updated 77 it is converted to a phase value 84 by the microprocessor and the drive signal is again monitored for a low going edge 67.

In summary, if the electrical signal 21 is low, the phase difference is represented by the time until the electrical signal 21 goes high. If the electrical signal 21 is high when the drive signal 13 goes high, the phase difference is represented by the time until the electrical signal 21 goes low and then high again. The algorithm shown by the state diagram in FIG. 3 will handle the situation where the electrical signal 21 is either leading or lagging the drive signal 13 by 180 degrees or less. Although in this particular embodiment, triggering events comprise detected low going and high going edges as described above, it would be readily apparent to one of ordinary skill in the art that other triggering events could also be used, such as switching all of the triggering events for low going edges to high going edges and all of the triggering events for high going edges to low going edges.

Figure 7:
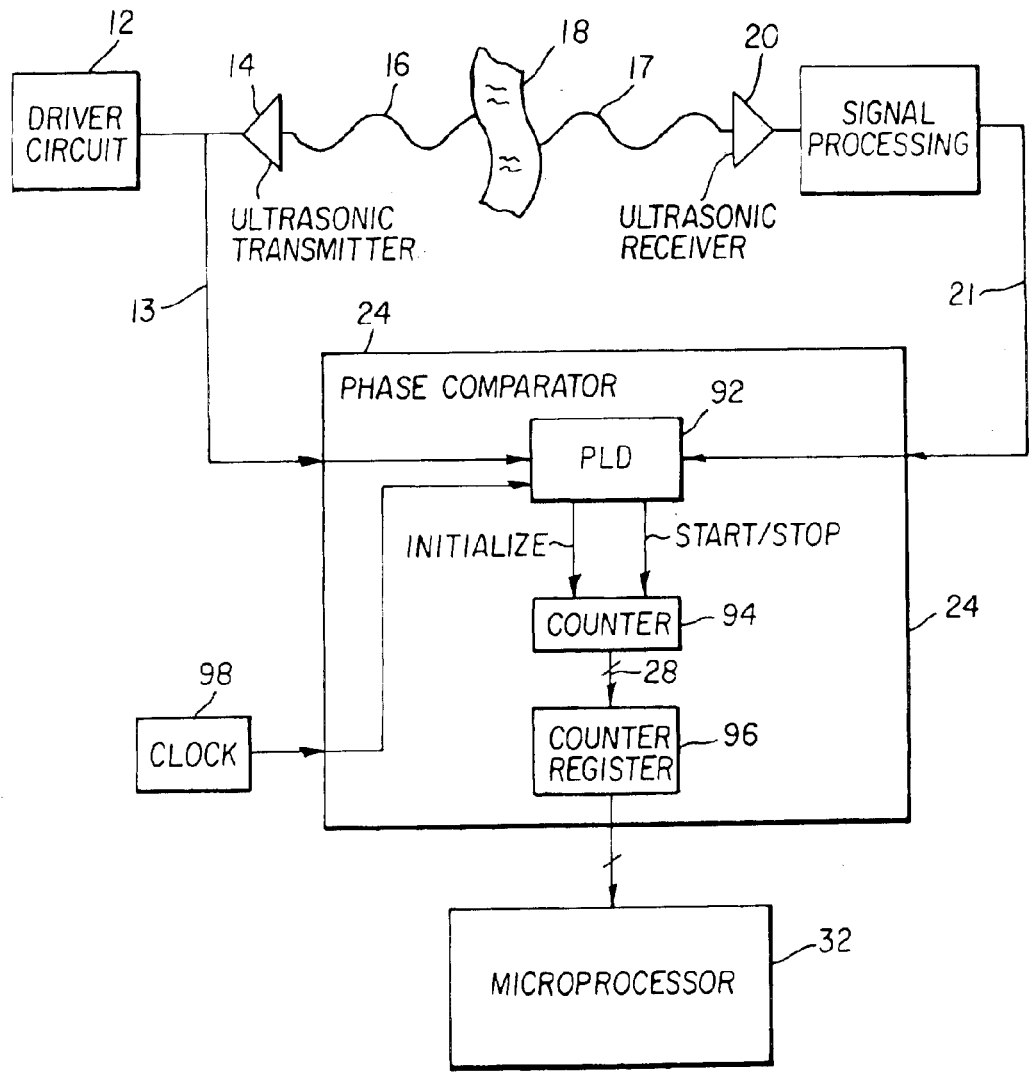
FIG. 7 is a block diagram of detection circuit including a detailed block diagram of the phase comparator circuit in accordance with another embodiment of the present invention.

In this particular embodiment, the sample rate is controlled by a clock 98 shown in FIG. 7. Using a faster clock will increase the sample rate and hence the resolution and accuracy. The counter measures the number of clock pulses. Since a digital value of the time difference is obtained by reference to the counter, this value can be input directly into a microprocessor 32 or any digital logic unit for easy processing. This method will provide a full 360 degrees of phase shift measurement before phase wrap around occurs.

Figure 6:
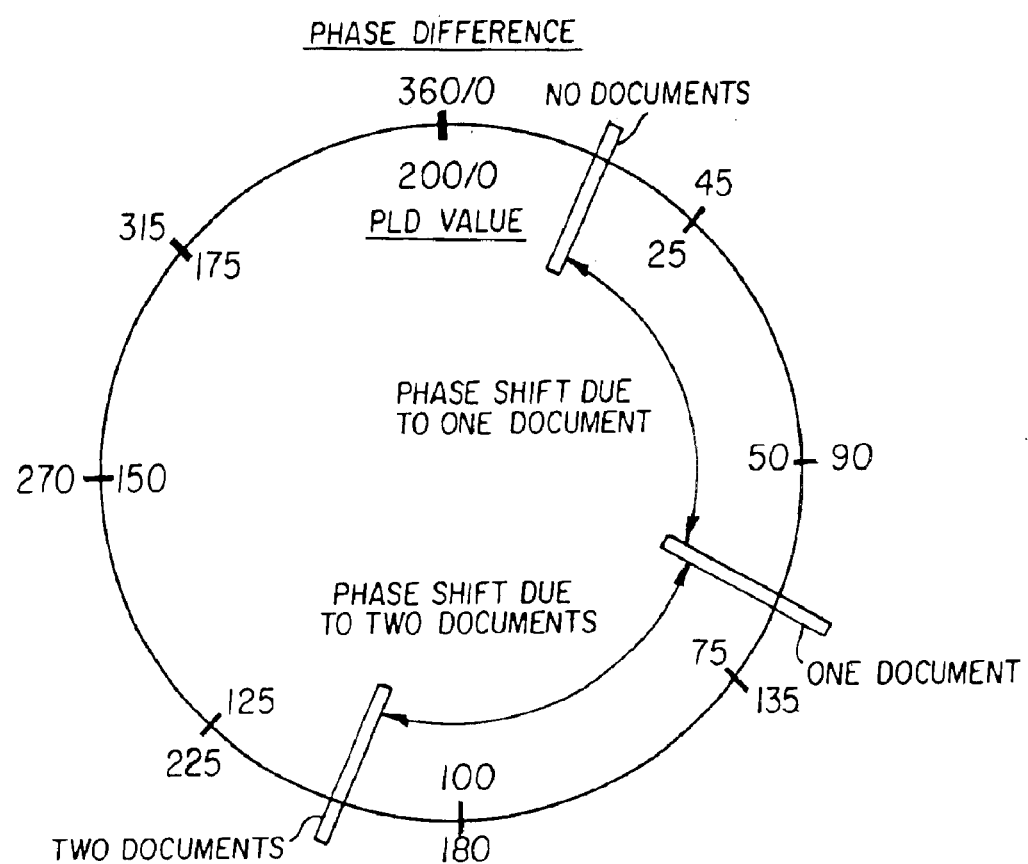
FIG. 6 is a schematic diagram of a phase shift between a driver signal and an electrical signal.

As applied to detection of multiple documents, the phase shift indicates the presence of more than one document. Referring now to FIG. 6 essentially no phase shift will occur when no documents are present. The presence of one document causes a phase shift of approximately 90 degrees. If two documents are present the phase shift will be approximately 180 degrees with some margin of error. A number of factors cause variation in the exact phase difference for two documents, some of which include thickness of the documents, angle of the transmitter and receiver, and angle of the document within the ultrasound path. This invention provides a method of obtaining reliable and inexpensive measurement of the presence of multiple documents, wherein the phase shift may exceed 180 degrees.

FIG. 7 shows additional details of the phase comparator 24 in accordance with another embodiment of the present invention. In this particular embodiment, the programmable logic device (PLD) 92 incorporates the algorithm shown in FIG. 3. The PLD starts and stops counter 94 according to the criteria described above with reference to FIG. 4. The counter values are transferred to the counter register 96 at the completion of a phase measurement cycle. Microprocessor 32 periodically samples counter register 96. The rate of sampling by the microprocessor 32 may be set at different values however, for example, a low volume document transport system may sample 2000 times per second. Clock 98 provides a sample rate signal to counter 94 and PLD 92. Clock rate 98 may sample at a rate of 32 μsec although other clock rates are available as described above. As the above-described method and system illustrate, the phase shift difference between the drive signal 13 and the electrical signal 21 can be obtained using only digital methods.

Due to vibrations, temperature changes, or usage, the distance between a transmitter and a receiver may change over time. It is therefore necessary to periodically calibrate the system to compensate for these changes. In other applications it is desirable to have the signal at the receiver in phase with the transmitted signal in order to eliminate some electrical components and reduce the cost of the apparatus. This invention is a means for performing calibration of an ultrasonic phase detection system electronically.

Figure 8:
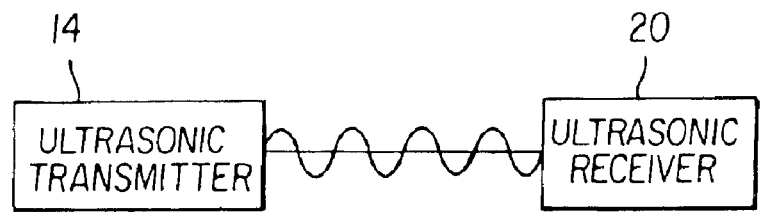
FIG. 8 is a diagram of a detector and a receiver where a transmitted signal and a received signal are in phase.

Referring to FIG. 8, an ultrasonic transmitter 14 and an ultrasonic receiver 20 are shown with a received signal at the receiver 20 which is in phase with the transmitted signal. Although in these and other examples discussed in this application ultrasonic signals, as well as transmitters and receivers which operate in the ultrasonic range are discussed, other types of signals which operate in other frequency ranges along with components which can operate in these different ranges can also be used.

Figure 9:
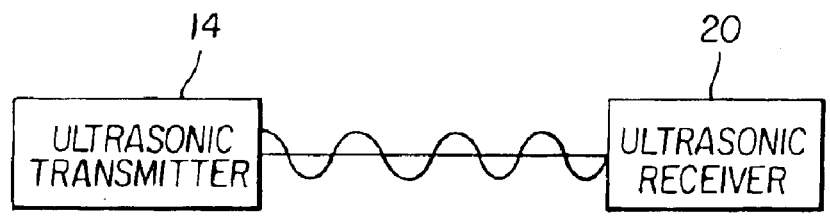
FIG. 9 is a diagram of the detector and the receiver where the transmitted signal and the received signal are out of phase.

Referring to FIG. 9, another ultrasonic transmitter 14 and ultrasonic receiver 20 are shown with a received signal at the receiver 20 which is out of phase with the transmitted signal. Historically, this phase lag would be compensated for with a mechanical adjustment of the position of either or both of the transmitter 14 and receiver 20. Unfortunately, this was a difficult process to do accurately and was time consuming. With the present invention, the phase of the transmitted and received signals can be adjusted or calibrated to be substantially in phase or in phase within a set amount much more easily and more accurately than prior techniques and without any mechanical adjustment of the transmitter 14 or receiver 20.

Figure 10:
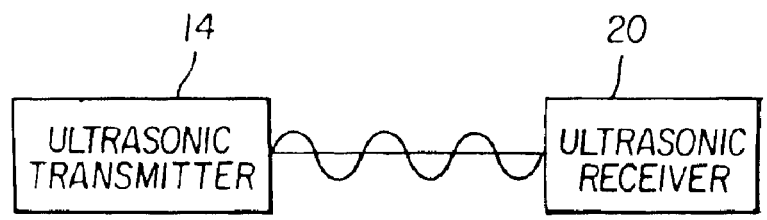
FIG. 10 is a diagram of the detector and the receiver where the frequency of the transmitted signal has been increased so that the transmitted signal and the received signal are in phase.
Figure 11:
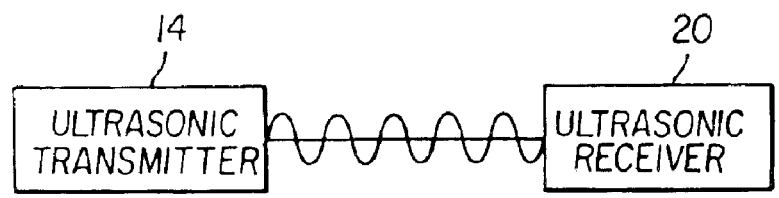
FIG. 11 is a diagram of the detector and the receiver where the frequency of the transmitted signal has been increased so that the transmitted signal and the received signal are in phase.

Referring to FIG. 10, one example where the out of phase condition shown in FIG. 9 has been corrected by decreasing the frequency of the transmitted signal output by the transmitter 14 is illustrated. Referring to FIG. 11, another example wherein the out of phase condition shown in FIG. 9 has been corrected by increasing the frequency of the transmitted signal output by the transmitter 14 is illustrated. In both of these examples, the phase of the transmitted and received signals has been calibrated without any mechanical movement of either the transmitter 14 or the receiver 20.

Referring to FIG. 12, a circuit 31 for adjusting phase in accordance with one embodiment of the present invention includes a transmission system. In this particular embodiment, the transmission system includes a variable oscillator 11 coupled to a driver or drive circuit 12 which is coupled to a transmitter 14, although other types of components can be used for the transmission system. The variable oscillator 11 in conjunction with the driver 12 adjusts the frequency of the transmitted signal 16 transmitted by the transmitter 14, which is an ultrasonic transducer in this particular example although other types of transmitters can be used.

The circuit 31 also includes a receiving system which in this particular embodiment includes a receiver 20 coupled to an optional noise processor 22, although other types of components can be used for the receiving system. The receiver 20 captures or receives the transmitted signal and the noise processor 22 removes some or all of the noise from the received signal. Since methods and systems for removing noise from a signal are well known to those of ordinary skill in the art, they will not be discussed here.

The circuit 31 also includes a phase adjustor which in this particular embodiment includes a phase comparator 22 and a phase adjustment processor 25, although other types of components can be used for the phase adjustor. The phase comparator 22 is coupled to the transmission system, the receiving system, and the phase adjustment processor 25. The phase adjustment processor is coupled to the transmission system The phase comparator 22 compares the phase of the received signal 17 and the transmitted signal 16 and provides a determined phase difference between the two signals. The phase adjustment processor 25 changes the frequency of the transmitted signal 16 output by the transmission system in response to the determined phase difference.

The operation of the circuit 31 will be discussed with reference to FIGS. 8–12. To calibrate the circuit 31 to correct or adjust for a phase difference between the transmitted signal 16 and the received signal 17, first the transmitter 14 and/or the receiver 20 are placed in their designated locations, e.g. for detection of multiple documents, or are repositioned. Next, before any adjustment or calibration can take place, there are no objects located between the transmitter 14 and the receiver 20.

Next, in this particular embodiment the variable oscillator 11 outputs a signal to the driver 12 which outputs a drive signal 13 to the transmitter 14 which outputs or transmits a transmitted signal 14 at a frequency determined by the variable oscillator 11 and driver 12. A received signal 17 resulting from the transmitted signal 16 is captured or received by the receiver 20 and is converted to an electrical signal 21.

Next, in this particular embodiment the noise processor 22 reduces and/or removes unwanted electrical noise from the electrical signal 21 and outputs an electrical signal 23. Electrical signal 23 which represents the received signal 17 and a drive signal 13 which represents the transmitted signal 16 are coupled to the phase comparator 24 for a phase comparison, although the electrical signal 23 could be compared against other signals, such as a set reference signal.

In this particular embodiment, the phase comparator 24 compares the electrical signal 23 and the drive signal 13 and determines a phase difference between the transmitted signal 16 and the received signal 17. As shown in FIGS. 8 and 9, the transmitted signal 16 and the received signal 17 may be in phase or out of phase.

Next, in this particular embodiment the determined phase difference is transmitted to the phase adjustment processor 25 which processes the determined phase difference and adjusts variable oscillator 11 to change the frequency of driver 12, thus changing the frequency of the transmitted signal 16 transmitted by the transmitter 14. This adjustment or change in the frequency of the transmitted signal 16 results in a phase change of the received signal 17.

In one embodiment of the invention, the frequency of the transmitted signal 16 from transmitter 14 is adjusted upward or downward depending on whether the phase of the received signal 17 is greater than, i.e. lagging, or less than, i.e. leading, the transmitted signal 16. For a phase which is greater than the transmitted signal 16, the adjustment to the frequency of the transmitted signal 16 output by the transmitter 14 will be increased. For a phase which is less than the transmitted signal 16, the adjustment to the frequency of the transmitted signal 16 output by the transmitter 14 will be decreased.

In one particular embodiment, if the determined phase difference between the phase of the transmitted and received signals 16 and 17 is less than a first set phase difference, then no change is made to the transmitted signal 16 output by the transmitter 14. Preferably, the first set phase difference is one degree. Thus, if the phase of the received signal 17 is no more than one degree out of phase with the phase of the transmitted signal 16 no change is made to the frequency. Although in this particular embodiment, the first set phase difference is one degree, other set phase differences can be used as necessitated or desired for the particular application, such as a set phase difference of substantially zero or two or more degrees. Once the phase between the transmitted signal 16 and the received signal 17 has been corrected or calibrated to fall at or below the desired difference in phase between the signals, the phase correction circuit and method are stopped. Periodically, a phase correction using the present invention can be carried out between detecting document feeds for multiple documents, if needed or desired.

One of the advantages of the present invention is that it is possible to correct the phase without any mechanical manipulation of the transmitter 14 or receiver 20 location. Additionally, the present invention provides for automatic and dynamic phase compensation for things such as wear and temperature changes. A maximum of 360 degrees of phase shift can be measured before phase wrap around occurs. After calibration, a phase change measurement of the full 360 degrees can be measured since the reference phase difference is adjusted to zero. The electronic calibration allows this full range to be maintained by performing a dynamic calibration.

By utilizing an electronic calibration instead of a mechanical calibration, the cost to perform the calibration is reduced and the accuracy is maintained without requiring physical adjustments.

The invention has been described in detail with particular reference to certain preferred embodiments thereof, but it will be understood that variations and modifications can be effected within the scope of the invention. For example, although the invention has been described as applied to a system for detecting phase shift in an ultrasonic application, the invention can be applied more broadly to any system for detection of changes in the phase of signals. In the broader sense the drive signal can be any reference signal and the electrical signal will be the resulting signal after some perturbation causing a phase shift. Although the invention has been discussed with reference to calibrating a transmitter and receiver to achieve an in phase condition at the receiver the invention is applicable to calibrations where a fixed phase difference between the transmitter and receiver is desirable.

Parts List

10. Apparatus
11. Variable oscillator
12. Ultrasonic drive circuit
13. Drive signal
14. Ultrasonic transmitter
16. Ultrasonic signal
17. Ultrasonic signal
18. Document feed
20. Ultrasonic receiver
21. Electrical signal
22. Signal processor
23. Electrical signal
24. Phase comparator
25. Signal processor
26. Phase difference signal
28. Information signal
32. Microprocessor
42. Sheet feeding device
48. Stack support
50. First portion
52. Housing
54. Feed module
56. Second portion
66. Separator
67. Sample drive signal
68. Sample drive signal
70. Counter initialized
71. Low going level detected
72. High going edge determined
73. Counter started
74. Electrical level not high
75. High going edge detected
76. Counter stopped
77. Counter register updated
78. Low going edge detected
79. High going edge detected
80. Counter stopped
81. Counter register value updated
82. Path less than 180 degrees phase difference
83. Path more than 180 degrees phase difference
84. Convert actual phase value
87. Sample electrical signal
88. Sample electrical signal
89. Sample electrical signal
90. Sample electrical signal 92. PLD
94. Counter
96. Counter register
98. Clock

What is claimed is:

1. A method for adjusting phase comprising:

determining a phase difference between a transmitted signal and a received signal resulting from the transmitted signal;

adjusting a frequency of the transmitted signal in response to the determined phase difference so that an adjusted phase difference between the transmitted signal and the received signal is less than a first set phase difference;

wherein the step of adjusting further comprises:

initiating when the adjustments to the frequency of the transmitted signal can be made; and discontinuing any further of the adjustments to the frequency of the transmitted signal when the determined phase difference is less than the first set phase difference.

2. A method as in claim 1 wherein said frequency of said transmitted signal is adjusted to a higher frequency.

3. A method as in claim 2 wherein said frequency is adjusted by an incremental step of no more than 0.05 percent of said frequency.

4. A method as in claim 1 wherein said frequency of said transmitted signal is adjusted to a lower frequency.

5. A method as in claim 4 wherein said frequency is adjusted by an incremental step of no more than 0.05 percent of said frequency.

6. A method as in claim 1 wherein said transmitted signal is a digital signal.

7. A method as in claim 1 wherein said transmitted signal is an analog signal.

8. A method as in claim 1 wherein said first set phase difference is 1 degree of phase difference.

9. The method as set forth in claim 1 wherein the first set phase difference is one degree.

* * * * *